(12) United States Patent
Boiten et al.

(10) Patent No.: US 10,646,357 B2
(45) Date of Patent: May 12, 2020

(54) JOINTLESS PROSTHETIC FOOT (71) Applicant: OTTO BOCK HEALTHCARE GMBH, Duderstadt (DE)

(72) Inventors: Herman Boiten, Gottingen (DE); Jens Northemann, Duderstadt (DE); Andrea Cremer, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 59 days.

(21) Appl. No.: 15/305,647

(22) PCT Filed: May 8, 2015

(86) PCT No.: PCT/DE2015/100187
§ 371 (c)(1),
(2) Date: Oct. 20, 2016

(87) PCT Pub. No.: WO2015/172767
PCT Pub. Date: Nov. 19, 2015

(65) Prior Publication Data
US 2017/0049585 A1 Feb. 23, 2017

(30) Foreign Application Priority Data
May 12, 2014 (DE) ........................ 10 2014 006 744

(51) Int. Cl.
*A61F 2/66* (2006.01)
*A61F 2/78* (2006.01)
*A61F 2/50* (2006.01)

(52) U.S. Cl.
CPC .................. *A61F 2/66* (2013.01); *A61F 2/78* (2013.01); *A61F 2002/5007* (2013.01);
(Continued)

(58) Field of Classification Search
CPC ...... A61F 2002/5018; A61F 2002/5079; A61F 2002/6671; A61F 2002/6657–6692
See application file for complete search history.

(56) References Cited

U.S. PATENT DOCUMENTS

| 4,636,220 A | 1/1987 | Ziegelmeyer |
| 5,112,356 A | 5/1992 | Harris et al. |

(Continued)

FOREIGN PATENT DOCUMENTS

| EP | 0793949 A1 | 9/1997 | |
| FR | 2.148.322 | * 3/1973 | ............... A61F 2/66 |

(Continued)

OTHER PUBLICATIONS

Computer generated translation of Pisani, FR 2 626 463 A1, published on Aug. 4, 1989.*

(Continued)

*Primary Examiner* — David H Willse
(74) *Attorney, Agent, or Firm* — Holland & Hart, LLP (57) ABSTRACT

A jointless prosthetic foot having a leaf spring which has a distal footfall section, a connecting section and a proximal attachment section which extends in an anterior-posterior direction and to which an attachment adapter can be fixed. The attachment adapter is mounted such as to be movable along a convexly curved path in the anterior-posterior direction.

24 Claims, 12 Drawing Sheets

(52) U.S. Cl.
CPC ............... *A61F 2002/5018* (2013.01); *A61F 2002/5021* (2013.01); *A61F 2002/5083* (2013.01); *A61F 2002/6614* (2013.01); *A61F 2002/6621* (2013.01); *A61F 2002/6642* (2013.01); *A61F 2002/6671* (2013.01)

(56) References Cited

U.S. PATENT DOCUMENTS

| | | | |
|---|---|---|---|
| 5,116,383 A | * | 5/1992 | Shorter ............... A61F 2/66 623/49 |
| 5,376,141 A | * | 12/1994 | Phillips ............... A61F 2/66 623/38 |
| 5,653,767 A | * | 8/1997 | Allen ............... A61F 2/66 623/52 |
| 5,653,768 A | | 8/1997 | Kania |
| 5,897,594 A | | 4/1999 | Martin et al. |
| 7,520,904 B2 | | 4/2009 | Christensen |
| 8,535,390 B1 | | 9/2013 | Lecomte et al. |
| 2006/0030950 A1 | | 2/2006 | Townsend et al. |
| 2006/0241782 A1 | * | 10/2006 | Curtis ............... A61F 2/66 623/55 |
| 2009/0082878 A1 | | 3/2009 | Christensen |

FOREIGN PATENT DOCUMENTS

| | | | |
|---|---|---|---|
| FR | 2626463 A1 | | 8/1989 |
| JP | H1-310660 A | | 12/1989 |
| JP | H9-327473 A | | 12/1997 |
| SU | 778732 | * | 12/1980 ............... A61F 2/66 |

OTHER PUBLICATIONS

Babbitt—Competitor magazine, Sep. 2010, p. 16.*
PCT International Search Report for PCT International Patent Application No. PCT/DE2015/100187, dated Jul. 31, 2015.

* cited by examiner

JOINTLESS PROSTHETIC FOOT

TECHNICAL FIELD

The invention relates to a jointless prosthetic foot with a leaf spring which has a distal foot-strike section, a connecting section, and a proximal attachment section which extends in an anterior-posterior direction and on which an attachment adapter can be secured. A prosthetic foot of this kind is suitable in particular as a sports foot.

BACKGROUND

A sports foot is generally designed as a one-piece leaf spring made from a fiber-reinforced plastic. The binding to a socket, which is also intended to be possible in below-knee prostheses, has the effect that, during loading, the tip of the leaf spring not only moves upward with respect to the socket, i.e. in the vertical direction, but also moves forward as a result of a flexion of the spring. When the foot is set down, this has the effect that the leg is pressed rearward in relation to the ground. Moreover, when the energy stored in the spring is released, a posteriorly directed component may arise, with the result that the direction of the energy release does not correspond 100% to the direction in which the athlete is running.

Under the trade name Flex-Run, the company Össur markets a sports foot with a spring which is bent in a C shape and on the upper end of which an attachment adapter is secured.

Under the trade name "endolite Blade XT", the company Chas A Blatchford & Sons Ltd. markets a prosthetic foot for amateur athletes and runners, having a forefoot spring which has a substantially horizontal head section and a one-piece spring with an outwardly convex shape, said spring being divided into two parts in the lower area by a slit. In the front area of the spring, a sole protection and a heel spring are fastened by way of two screws; the spring stiffness of the heel spring can be set using a wedge. The heel spring has a less flexible reaction as a consequence of inserting the heel wedge. A proximal adapter is guided displaceably in a receiving slit in a securable manner.

The company Freedom Innovations markets a sports foot under the trade name "Nitro Running Foot", with a vertical receiving area on which a proximal adapter is secured. From the proximal adapter, a one-piece leaf spring extends in an arc shape as far as a foot-strike area. The special leaf spring slopes gently upward.

SUMMARY

The object of the present invention is to make available a prosthetic foot which is easily adaptable to the different needs of a user, and to bring the action line closer to the center of gravity of the body, so as to allow the prosthetic foot to be used as efficiently as possible.

According to the invention, this object is achieved by a jointless prosthetic foot having the features of the main claim. Advantageous embodiments and developments of the invention are disclosed in the dependent claims, the description and the figures.

In the jointless prosthetic foot with a leaf spring which has a distal foot-strike section, a connecting section which can extend obliquely upward and rearward, and a proximal attachment section which extends in an anterior-posterior direction and on which an attachment adapter can be secured, provision is made that the attachment adapter is mounted so as to be adjustable along a convexly curved path in the anterior-posterior direction. By means of the adjustable, preferably steplessly adjustable, mounting of the attachment adapter along a path which is convex, i.e. curved outward, it is possible that, during a shift of the attachment adapter relative to the leaf spring in the anterior-posterior direction, the position of the foot-strike area or of the foot-strike line to the perpendicular of the attachment adapter remains substantially constant, i.e. there is no displacement of the foot-strike area in the anterior-posterior direction. It is thus possible to bring about an increased variability of the force introduction on account of the change of the force lever, without changing the set-up of the prosthesis. In particular, upon displacement of the leaf spring in the anterior direction, no shifting of the foot-strike area is effected in the anterior direction to the center of gravity of the body, which would lead to a displacement of the line of action in front of the center of gravity of the body, by which means the person using the prosthesis would be slowed down. Moreover, in addition to the constant or almost constant position of the foot-strike area and the avoidance of an increased rearwardly directed force component, the prosthetic foot height must be maintained, as a result of which the user senses no appreciable change in the prosthesis dimensions despite the change in the spring properties.

In the case where the attachment adapter is mounted directly on the leaf spring, the attachment section can have a directly convex shape in order to configure the desired path curve. Upon adjustment under the adapter, the leaf spring is then displaced in the anterior or posterior direction, more easily to the front or rear, and the adapter is fixed in the desired position. If the adapter is secured on the leaf spring via an attachment adapter bearing, this can likewise permit a non-linear adjustment, such that an adjustment on the attachment adapter bearing alone or in combination with a non-linear configuration of the attachment section leads to a substantially constant prosthesis height at different positions of the attachment adapter on the leaf spring. Both the attachment section and also the attachment adapter bearing can be formed convexly, the attachment adapter bearing can have a curved guide path for the attachment adapter, wherein the curvatures of the attachment section and/or of the attachment adapter bearing do not have to be constant. The curvatures are configured or supplement each other in such a way that the attachment adapter itself remains at a substantially constant height during an adjustment, and the foot-strike area remains substantially unchanged during an adjustment. If the rotation point of the leaf spring in the foot-strike section lies in the perpendicular to the attachment adapter, and if the bearing surface of the foot-strike section has a constant curvature, then the curvature of the attachment section and/or the curvature of the attachment adapter bearing can be constant. If the foot-strike point or the foot-strike line lies in front of or behind the perpendicular, and if the foot-strike section in the roll-over area, for example, is provided with a constant radius of curvature during the adjustment, the curvature of the attachment section and/or of the attachment adapter bearing is such that the height difference is compensated, the prosthetic foot height remains constant, and the foot-strike point or the foot-strike line as before lies in front of or behind the perpendicular. The set-up does not change.

In the attachment section and/or the attachment adapter bearing, a receiving slit extending in the anterior-posterior direction can be arranged or formed for the attachment adapter. By virtue of the arrangement of the receiving slit in the attachment section or in the attachment adapter bearing, it is possible to achieve increased variability of the force introduction on account of the change of the force lever, with at the same time stepless displaceability and good guiding precision. Besides a receiving slit, the attachment adapter can be secured on a guide web or directly on the leaf spring, for example by a clamping connection.

The path, on which the attachment adapter is in particular mounted displaceably, can at least regionally have a radius of curvature which opens out in the foot-strike section, preferably in the roll-off area during the adjustment of the leaf spring. If the roll-off point or the roll-off line in the foot-strike section coincides with the center point of the curvature, the radius forms the shape of the path curvature along which the attachment adapter can be displaced.

In an advantageous embodiment, provision is made that the connecting section has a concave shape such that, after the foot-strike section, the leaf spring curves away from the ground, which has the effect that the connection area cannot come into contact with the ground, even with an increased length of stride. The ground contact of the leaf spring thus takes place only in the foot-strike section, not in the posteriorly and proximally adjoining connecting section. It is thus possible to keep the connecting section free from any ground contact, such that a defined assignment of the respective functions in the respective sections can be established. The foot-strike section is the only area that has ground contact, the attachment section defines the allocation of the attachment adapter to the leaf spring, and the connecting section produces the resilient, posteriorly and proximally extending connection between these two sections. By virtue of the convex shape of the attachment section, it is possible, during a rotation about the foot-strike point or the foot-strike line in the convex foot-strike section curved outward in the direction of the arc, to bring about an increase or decrease of the lever length of the leaf spring, without the foot height or the position of the foot-strike area being changed. If a greater lever length is wanted, for example in order to permit gentler spring compression during light jogging, the attachment adapter is displaced forward; if the attachment adapter is displaced further rearward, the spring stiffens, which is preferable for sprinting. Thus, seen from the attachment adapter, the preferred profile of the leaf spring is initially shaped convexly upward and away from the ground, then in the connecting section it is shaped concavely away from the ground and, finally, is shaped convexly toward the ground in the foot-strike section, in order there to provide a defined rotation point or a defined rotation axis in the bearing area of the foot-strike section which, on account of the convex configuration of the displacement path of the attachment adapter, remains almost unchanged relative to the perpendicular of the attachment adapter. The concave connecting section ensures that the ground contact always takes place in the front foot-strike section. If, with a strongly angled foot strike, the connecting section first had ground contact, the working lever of the prosthetic foot would be greatly reduced, as a result of which the prosthetic foot would be much stiffer at set-down than when lifting the prosthetic foot at the end of the ground contact. Such behavior is undesirable and is prevented by the concave curvature posterior to the foot-strike section.

In a development of the invention, provision is made that the attachment section, at least in the area of the receiving slit, has a radius of curvature which is constant with respect to a roll-off area in the foot-strike section, such that a constant foot height can be maintained independently of the position of the attachment adapter. The roll-off area is that area which, during the adjustment of the attachment adapter, is traversed from a maximum anterior point to a maximum posterior point, when the prosthetic foot is unloaded or only statically loaded, e.g. when the person using the prosthesis is standing relaxed. The constant radius of curvature can be achieved by the fact that the radii of the attachment section and of the foot-strike section are identical, or by the fact that approximately the roll-off area is so narrow that there is no significant change of the prosthesis height. This ensures that there is a constant prosthetic foot height across the adjustment range of the receiving slit.

On the attachment section, e.g. on the receiving slit, on the leaf spring, on the attachment adapter bearing and/or on the attachment adapter, a scale for orientation of the anterior-posterior adjustment of the attachment adapter can be arranged, for example by line markings and a corresponding marking on the attachment adapter, such that, by means of the scale, a relationship to the achieved degree of hardness is produced in a quantifiable manner. It is thereby possible to adjust the hardness of the spring, and therefore also the prosthetic foot as such, not only by feel, but also exactly according to measured parameters. The scale or marking can have a Vernier. The scale permits a reproducibility of the setting.

The leaf spring is preferably thicker in the attachment section than in the foot-strike section, in order to achieve a precise assignment of the attachment adapter to the prosthesis socket and to the leaf spring. On account of the increased stiffness, which derives from an increased leaf spring thickness resulting from an increased number of fabric layers and/or an additional plastic matrix composition, only a slight deformation is permitted in the attachment section.

The receiving section is advantageously stiffer, as far as the transition to the connecting section, than in the connecting section itself and than in the foot-strike section. The stiffer configuration, which can extend to before the rear curvature or the rear arc, has the effect that the leaf spring deforms only slightly in this area, in order to cause the least possible horizontal displacement of the line of action of the leaf spring. A deformation of the leaf spring in the area of the attachment section would result in an almost horizontal deformation of the prosthetic foot tip, which is undesirable. Only in the area of the rear convex arc is the leaf spring designed tapering, because a deformation here leads to a greatly reduced horizontal displacement of the line of action. A deformation in the connecting section with the concave configuration also leads to a relatively more vertical direction of action of the leaf spring and is therefore desirable. By means of the spring tapering from the attachment section toward the foot-strike section, it is possible for the mechanical loads inside the spring to be kept substantially constant, since a lower mechanical load arises at the front end of the spring, i.e. in the area of the foot tip, than in the area of the support in the attachment adapter. The stiff configuration of the leaf spring in the attachment section and the more flexible configuration starting from the end area of the attachment section is also to be seen as an independent invention irrespective of the adjustment path of the attachment adapter. The tapering or more flexible configuration of the spring begins in front of the rear arc and can increase as far as the foot tip. The increasingly more flexible configuration can be provided continuously or in discrete steps, for example regionally for the connecting section and the foot-strike section.

The attachment adapter is arranged in a receiving slit, on a receiving web or on the leaf spring, wherein the attachment adapter has a contact surface with a shape corresponding to the attachment section or to the respective securing component. This means that the attachment adapter is designed in several parts, preferably having an upper part and a lower part, which can have the effect that the parts have on the one hand a concave configuration and on the other hand a convex configuration, so as to be able to bear over the greatest possible surface area on the optionally curved shape of the attachment section or of the attachment adapter bearing.

The attachment adapter can consist at least of a first, preferably upper adapter part and a second, preferably lower adapter part, wherein both adapter parts have correspondingly shaped contact surfaces, thereby ensuring that the adapter parts bear over a large surface area on the leaf spring or the adapter bearing. If securing is effected on a web or in a slit formed therein, the adapter parts can also be arranged to the right and left of the web.

To be able to effect simple displacement across the entire adjustment range, the leaf spring is provided in the attachment section with a constant material thickness, such that a tilting of the attachment adapter on account of different material thicknesses, for example on account of a tapering leaf spring in the rear adjustment area, is ruled out. Lateral clamping can also take place directly on the leaf spring.

A sole contour element, which has at least one padding or a profiling, can be secured in the foot-strike section in order to protect the abrasion-sensitive leaf spring with a composite material against wear and, in addition, to make available improved traction for the person using the prosthetic foot. The sole contour element with padding or profiling advantageously covers the prosthetic foot tip in order, on the one hand, to provide protection of the fiber components specifically in the front surfaces of the leaf spring and, on the other hand, to protect the user against sharp splinters or the like.

The prosthetic foot tip protrudes anteriorly beyond the attachment section, such that the set-down point or strike point or strike line of the foot-strike section advantageously lies between 3 cm and 5 cm in front of the perpendicular line of the attachment adapter.

The length of the adjustment range, e.g. of the receiving slit or of the displacement path on the attachment section, advantageously permits a rotation of between 5° and 10°, which has proven sufficient to provide adequate variability within the prosthetic foot, without the spring length becoming too great and without the material thickness having to be too great in order to be able to take up the forces that occur upon still greater enlargement of the lever length.

The prosthetic foot can be realized with leaf springs in different degrees of hardness and different dimensions, such that it is suitable for patients of different weights and as a child's prosthetic foot. The prosthetic foot height can be chosen according to the body height and the amputation level or stump length. The course of the path along which the attachment adapter can be adjusted is preferably configured such that the height of the prosthetic foot remains substantially constant during an adjustment of the leaf spring relative to the attachment adapter in the anterior-posterior direction. On account of the preferably convex shape of the path, a rotation of the leaf spring takes place as the anterior proximal end of the leaf spring shifts along the adjustment path in the posterior direction, such that the strike point or the strike line of the leaf-shaped, advantageously likewise convexly shaped foot-strike section, which in this case is curved in the direction of the ground, migrates as it were in the anterior direction, such that, on the one hand, a constant prosthetic foot height or at least an almost constant prosthetic foot height is made available at a constant position of the foot-strike area. A substantially constant prosthetic foot height is considered as a maximum difference of less than 5% of the initial height of the foot.

The distance of the foot-strike section during the adjustment of the attachment adapter advantageously remains substantially constant with respect to the perpendicular line of the attachment adapter, in particular the strike point or strike area or the strike line, in order to have an unchanged or almost unchanged prosthesis set-up with a modifiable spring stiffness.

BRIEF DESCRIPTION OF THE DRAWINGS

Illustrative embodiments of the invention are explained in more detail below with reference to the attached figures, in which:

FIG. 2 shows a prosthetic foot with adapter;
FIG. 7 shows a perspective view of an attachment adapter.

DETAILED DESCRIPTION

Figure 1:
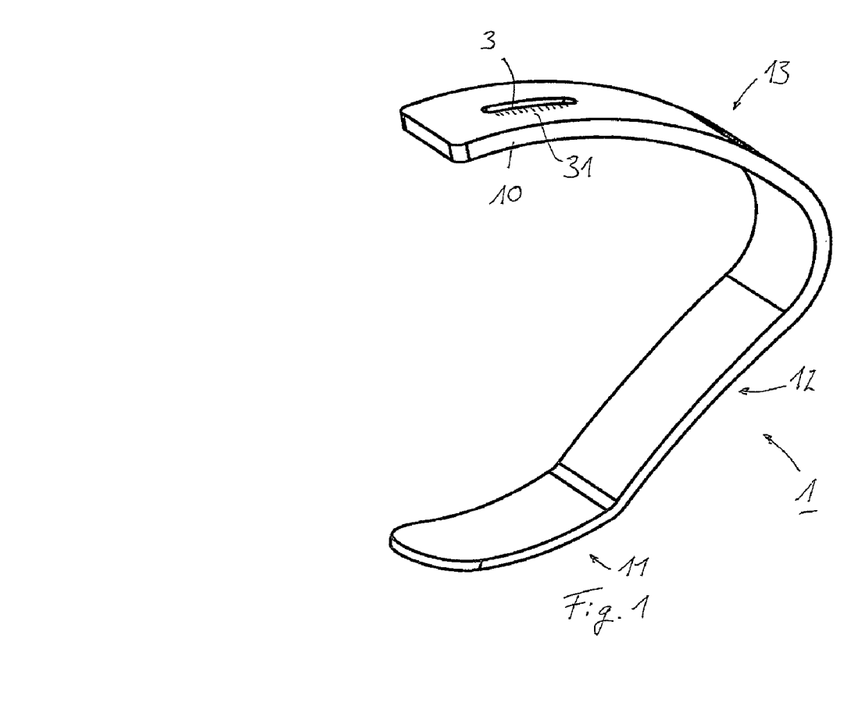
FIG. 1 shows a leaf spring of a prosthetic foot without adapter.

FIG. 1 shows a perspective oblique view of the prosthetic foot 1, which is composed of a one-piece leaf spring 10 and has a ground-side foot-strike section 11 arranged at the distal end of the leaf spring 10. The foot-strike section 11 is curved convexly toward the ground in order to permit a rolling movement during running. The foot-strike section 11 is adjoined by a concave connecting section 12 which is curved away from the ground and extends obliquely rearward and upward, i.e. in the proximal-posterior direction. By virtue of the concave design of the connecting section 12, the latter is kept away from ground contact when the foot is set down at an angle, for example during a pronounced forward movement of the prosthetic foot 1, such that, up to a set-down angle of 25°, exclusive contact is ensured in the foot-strike section 11. The proximal end of the connecting section is adjoined by an attachment section 13 which in turn has a convex shape, in this case curving away from the ground, wherein the direction of curvature of the attachment section 13 remains constant, whereas the radius of curvature can vary along the length of the attachment section 13. The radius of curvature decreases toward the rear end of the leaf spring 10, such that an arc forms, by way of which the leaf spring 10 extends further forward in the anterior direction as the profile continues.

A receiving slit 3 extending in the anterior-posterior direction is worked into or formed in the end area of the attachment section 13 and serves to receive the attachment adapter (not shown). In the area of the receiving slit 3, a scale 31 in the form of slits or markings is applied in order to orient the attachment adapter precisely and reproducibly.

The receiving slit 3 is substantially rectilinear and is formed centrally in the front end of the attachment section 13 as a through-slit.

The leaf spring 10 is formed in one piece from a fiber composite, in particular as a spring reinforced with carbon fibers. Fiber composites are generally produced from resin-impregnated fiber films, so-called prepregs, which are placed and oriented one over the other and are connected to each other by the action of heat.

In FIG. 2, the prosthetic foot 1 is shown with the attachment adapter 2 mounted in place. A marking 23 is arranged on the attachment adapter 2 and can be oriented with respect to the scale 31 or the markings on the attachment section 13. It will be seen in Figure that the foot-strike section 11 has a constant curvature and a convex, outwardly curved shape, and that the attachment section 13 extends forward in a roof shape from the proximal end of the connecting section 12. A stronger curvature is provided in the posterior area of the attachment section 13, so that the attachment section 13 can extend from the obliquely rearwardly extending connecting section 12 to above the foot-strike section 11. In the area of the receiving slit 3, the curvature of the leaf spring 10 is constant, likewise its material thickness. The material thickness of the leaf spring 10 decreases from the attachment section 13 to the connecting section 12 and again to the foot-strike section 11, where the leaf spring 10 is at its thinnest.

Figure 3:
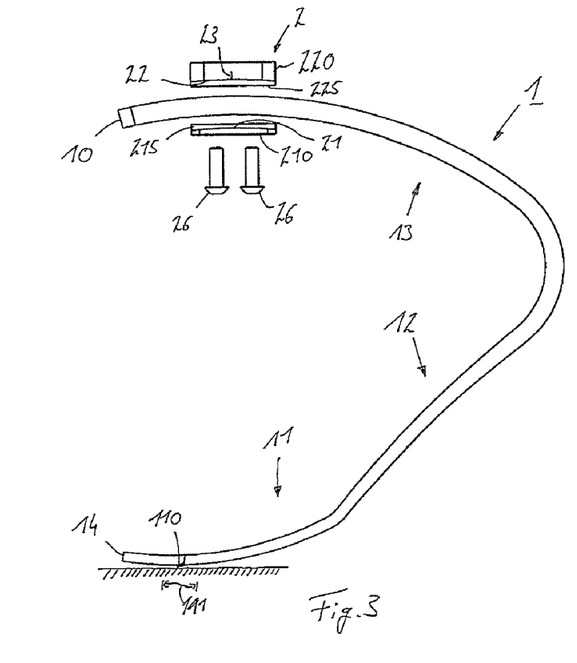
FIG. 3 shows an exploded side view of a prosthetic foot.

FIG. 3 shows an exploded side view of the prosthetic foot 1. The attachment adapter 2 is formed from an upper part 220 and a lower part 210, which can be connected to each other via two screws 26. The upper part 220 is provided with a marking 23 for orientation on the leaf spring 10. The contact surface 22 of the upper part 220 toward the upper face of the attachment section 13 has a curvature which corresponds to the curvature of the attachment section 13 and which has a concave shape matching the convex shape of the leaf spring in the attachment section 13. Accordingly, the contact surface 21 of the lower part 210 has a convex shape corresponding to the shape of the lower face of the attachment section 13. Both parts 220, 210 of the attachment adapter 2 have guide webs 215, 225, which correspond substantially to the width of the receiving slit 3 and prevent a rotation of the attachment adapter 2 inside the receiving slit 3.

The attachment adapter 2 lies above the foot-strike section 11 in the upright orientation of the prosthetic foot 1, wherein the attachment adapter 2 is located within the perpendicular projection of the foot-strike section 11. The foot tip 14 at the anterior and distal end of the leaf spring 10 is located in front of the attachment adapter 2, likewise the rollover area 111, which comes into contact with the ground and within which the set-down point 110 or the set-down line is located in a curved leaf spring 10.

Figure 3A:
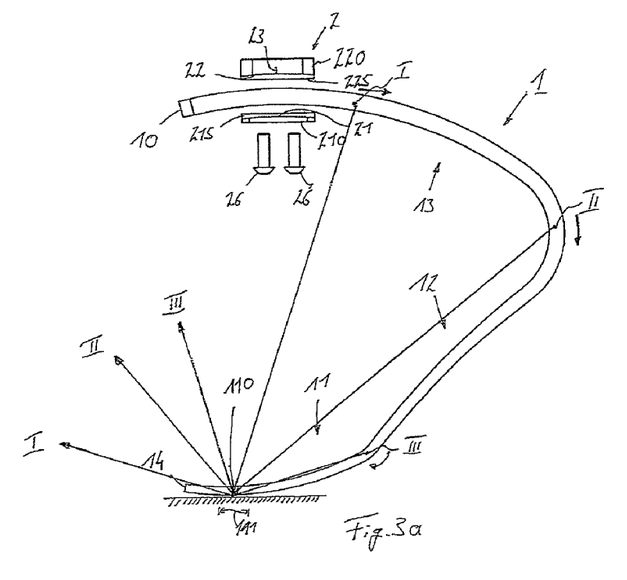
FIG. 3a shows a view of deformation directions.

The deformation direction of the leaf spring 10 is illustrated in FIG. 3a for deformations in different sections. When a deformation takes place in the attachment area about the point I, this leads to a deformation in a direction perpendicular or normal to the connecting line to the set-down point 110, as is represented by the arrow I. A deformation about the point I in the attachment section 13 negatively affects the deformation of the foot tip 14, since the deformation has an almost horizontal orientation. Therefore, the aim is for the leaf spring to be made as stiff as possible in this area, e.g. by an additional material thickness, spring width or corresponding material composition or fiber orientation. Only in the area of the rear arc is the spring made more flexible or thinner, since a deformation at the point II has a much less horizontal orientation, as can be seen from the arrow II. In this way, a lesser horizontal shift of the foot tip 14 is effected. A deformation in the connecting section 12 between the rear arc and the foot-strike section 11 can also deform, as is shown by the deformation at the transition to the foot-strike section 11 at point III. A deformation there leads to a predominantly vertical deformation of the foot tip 14; rearwardly acting force components are very slight. Therefore, the area of the leaf spring 10 from the adapter fastening as far as the entry to the rear arc is stiff, with an advantageously constant or almost constant thickness, whereas the distally adjoining areas of the leaf spring are more flexible, in particular thinner or narrower.

Figure 4:
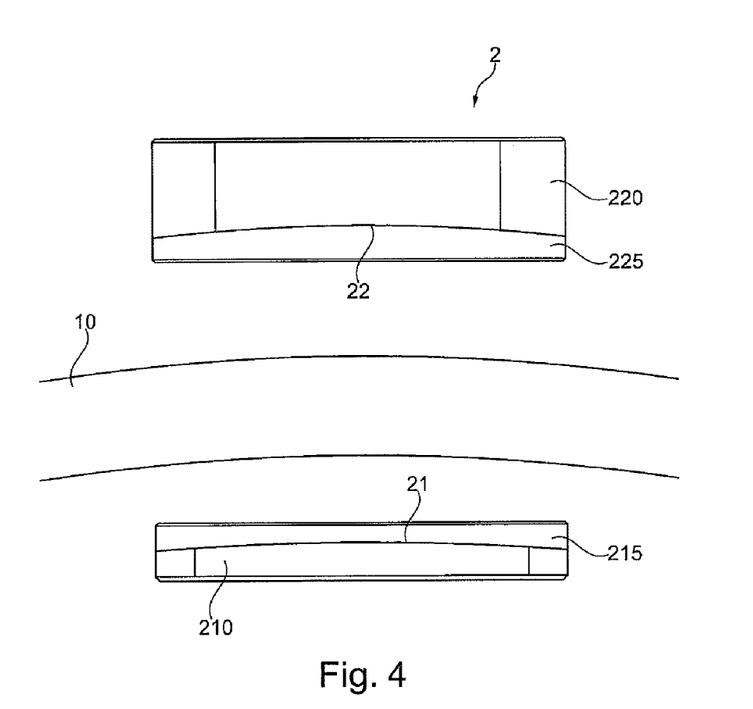
FIG. 4 shows a detailed side view of an adapter.

FIG. 4 shows an enlarged detailed view of the attachment adapter 2 with the upper part 220, the lower part 210, and the leaf spring 10 arranged between them in the attachment section 13. The leaf spring 10 has an upwardly convex curvature, and the contact surfaces 22, 21 of the upper part 220 and of the lower part 210 are designed respectively with a concavity or convexity corresponding to the surface of the attachment section 13, while the guide web 215, 225 is arranged centrally and corresponds in its width to the width of the receiving slit (not shown).

Figure 5:
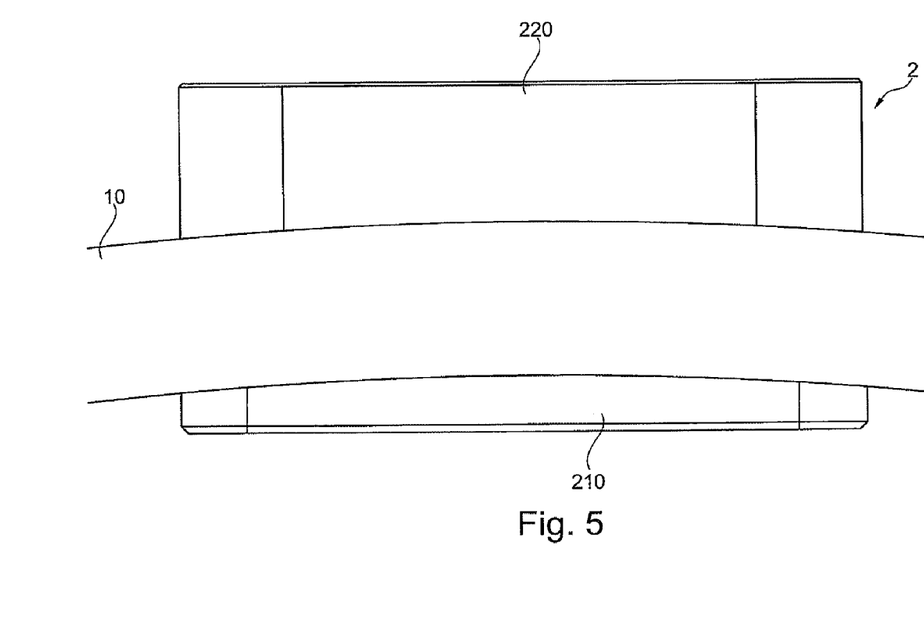
FIG. 5 shows a detailed side view of a mounted adapter.

FIG. 5 shows a side view of the mounted attachment adapter 2, with the contact surfaces resting flush on the respective surface of the leaf spring 10.

Figure 6:
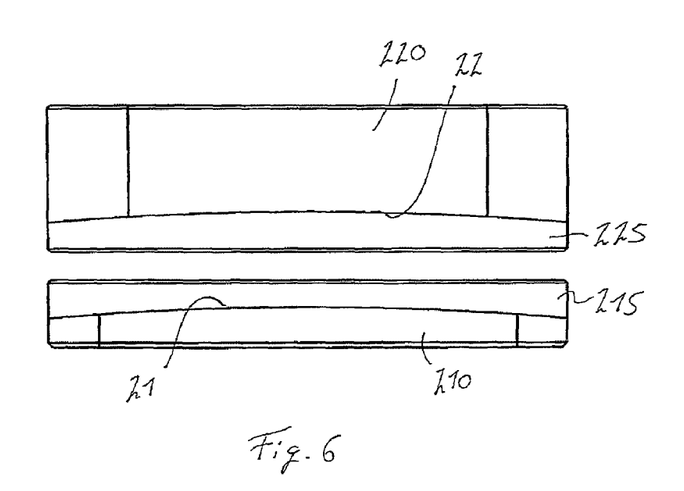
FIG. 6 shows a side view of two adapter parts.

FIG. 6 shows the attachment adapter 2 on its own in the unmounted state; the two components have a substantially rectangular configuration in the side view, and the surfaces of the guide webs 215, 225 lie parallel to each other.

FIG. 7 shows the attachment adapter 2 in the assembled state without the leaf spring; the convexly curved contact surface 21 of the lower part 210 can be seen, likewise the centrally arranged guide web 215, the flush arrangement of the upper part 220 and of the guide web 225 arranged thereon, and the two fastening screws 26 which extend through the guide webs 215, 225 and engage in a thread in the upper part 220. Threads 4 for securing further attachment means, for example adjustment cores, pyramid attachments or tubes, are provided on the upper part 220.

Figure 8:
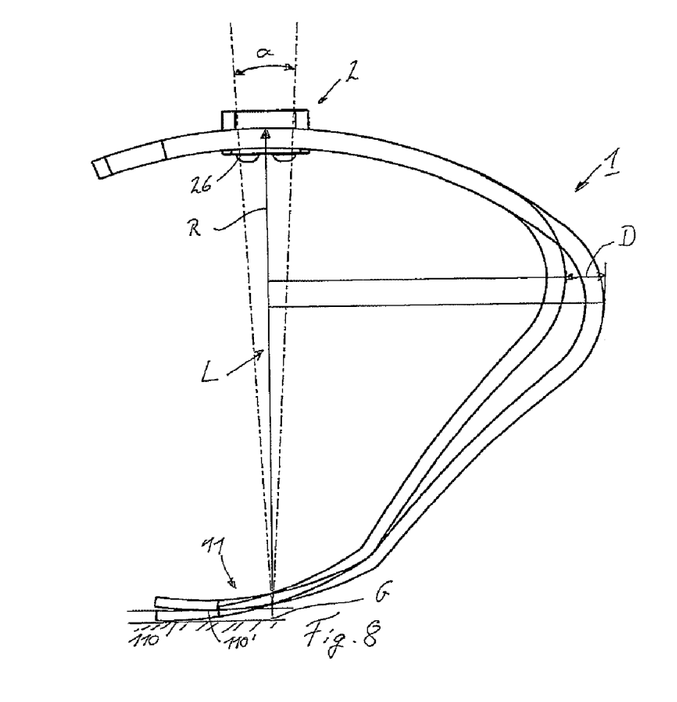
FIG. 8 shows a view of different settings of the leaf spring with respect to the attachment adapter.

FIG. 8 shows the prosthetic foot 1 in two different orientations. Starting from a perpendicular line L of the attachment adapter 2, the leaf spring 10 of the prosthetic foot 1 is pivotable through the angle α about the base point of the perpendicular line L, wherein the angle α represents the total length of the receiving slit 3. The total adjustment length can allow a rotation of between 5° and 10°, such that, starting from a central arrangement within the receiving slit 3, a tilting movement is possible, in the anterior direction and posterior direction, of up to 5° in each direction. The two illustrations show the leaf spring 10 in the position tilted furthest toward the front and in the position tilted furthest toward the rear. It will be seen from this that the lever length, i.e. the distance from the perpendicular force line L to the rear or posterior end of the attachment section 13, is different. When the leaf spring its tilted rearward, the lever increases, and, when the leaf spring is tilted forward, the lever decreases. The difference D between the front and rear positions is the difference of the lever length, such that the behavior of the leaf spring 10 can be adjusted via the effective levers.

The radius R of curvature of the attachment section 13 is constant, at least over the adjustment path of the attachment adapter 2. In the illustrative embodiment shown, the perpendicular line L and the base point of the perpendicular line L on the ground are used as reference variables. The set-down point 110 or 110' lies in front of the base point of the perpendicular line L in the running direction and in front of the projection of the attachment adapter 2 onto the ground. It will be seen that there is a slight height difference between the set-down points 110, 110'; this difference is generally negligible in practice and can be reduced or completely avoided if the radii R of the curvatures of the attachment section 13 and of the foot-strike section 11 match or if the set-down point 110 matches the base point of the perpendicular line L. It will also be seen that the set-down points 110, 110' remain at an almost constant distance in front of the perpendicular line L. In the case of a rectilinear configuration of the adjustment path of the attachment adapter 2, the set-down point would in each case migrate forward or rearward about the adjustment path.

Figure 9:
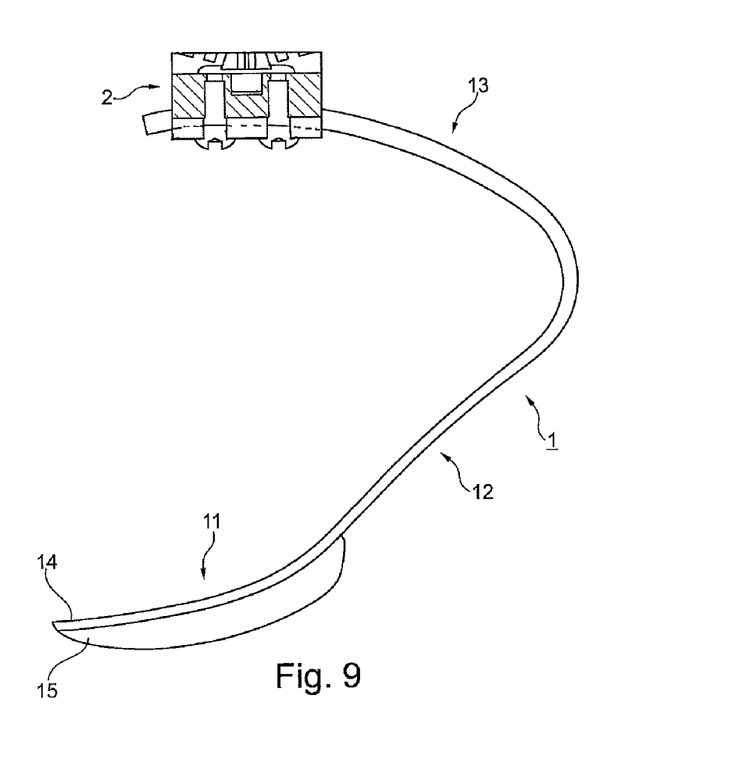
FIG. 9 shows a prosthetic foot with sole contour element.

FIG. 9 shows a complete prosthetic foot 1 with the leaf spring 10, the mounted attachment adapter 2, and a sole contour element with padding 15, which is arranged on the underside of the foot-strike section 11 and protrudes over and covers the foot tip 14 of the leaf spring 10 in the forward direction. By way of the sole profile element or padding 15, in which a profiling can also be incorporated, the position of the set-down point 110 can be determined for each position of the adjustment of the leaf spring. If the padding 15 is secured exchangeably on the leaf spring 10, individual adaptations can be easily performed by modifications to the padding, without changes to the leaf spring. During a displacement of the leaf spring along the convex path, there is no change in the height of the prosthetic foot 1 and no shifting of the set-down point 110, and therefore the prosthetic set-up is not changed despite the change in the elastic properties of the leaf spring 10.

Through the design of the leaf spring 10, it is possible to ensure that no rearwardly directed force component occurs during foot-strike, compression and rebound. Through the change in the lever arm on account of the displaceable mounting in a convex area of the attachment section, it is possible to change the compression behavior and rebound behavior of the leaf spring 10 and also the energy storage capacity in the manner desired by the person using the prosthetic foot. The lower rotation point can correspond substantially to the foot-strike point or the foot-strike line of the leaf spring in the foot-strike section, such that, with a corresponding radius of the curvature in the attachment section, a constant height of the prosthetic foot is made available.

The padding 15 can be screwed onto the foot-strike section 11 so that it can be easily replaced if it becomes worn. It will be seen from the side view according to FIG. 9 that the spring thickness decreases starting from the attachment section 13, in which the material thickness remains substantially constant, more precisely starting from the start of the rear arc as far as the foot tip 14. By virtue of the design according to the invention, the force introduction point and line of action of the spring remains substantially the same, independently of the length of the effective lever, since a rotation of the leaf spring takes place substantially about the foot-strike point or foot-strike line, together with a displacement of the attachment adapter 2, although the energy storage capacity of the leaf spring can be modified. By adjustment of the leaf spring 10, the angle of attack of the prosthetic foot can be changed, as a result of which a variation can take place, which deformation arises through the force vector, a deformation directed in the direction of the center of gravity of the body or in the horizontal direction.

Figure 10:
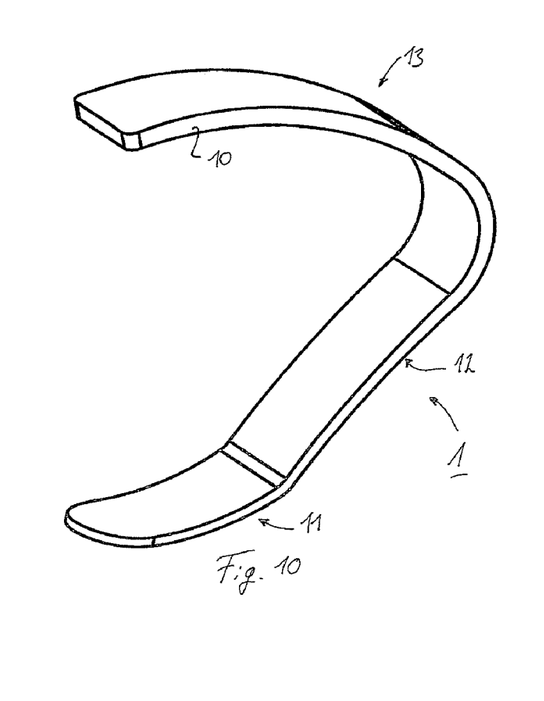
FIG. 10 shows a leaf spring on its own.

FIG. 10 shows a perspective view of the leaf spring 10 without attachment adapter. The attachment section is provided with a convex, outwardly directed curvature, which is designed corresponding to the convex, downwardly and outwardly directed curvature of the foot-strike section 11, such that an attachment adapter held, for example, by clamping on the attachment section 13 remains unchanged in height during the adjustment of the leaf spring 10 in the anterior-posterior direction, since the rolling action on the underside of the foot-strike section 10 is compensated by the curvature of the attachment section 13. The respective areas of the attachment section 13 and of the foot-strike section 11 involved then lie on a circular path or an approximated circular path, such that the prosthesis height or prosthetic foot height and the foot-strike section do not change. If the leaf spring only pivots about an axis and does not roll on a surface, the axis forms the rotation point and origin for the radius of curvature.

Figure 11:
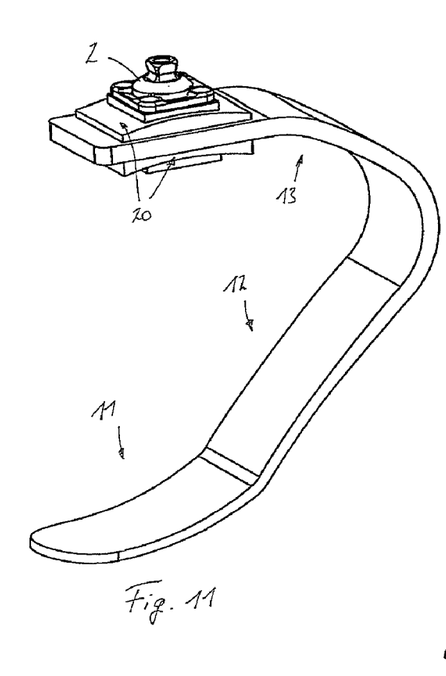
FIG. 11 shows a perspective view of a variant with attachment adapter bearing.

FIG. 11 shows a variant of the invention in a perspective oblique view. In the illustrative embodiment shown, the attachment section 13 is not curved; instead it is oriented substantially horizontally with respect to a ground surface (not shown). An attachment adapter bearing 20, which is designed in two parts, analogously to the design according to FIGS. 1 to 9, is arranged on the attachment section 13. The respective contact surfaces of the two parts of the attachment adapter bearing 20 are plane, such that they rest completely on the plane surface of the attachment section 13. Should the attachment section 13 have a curvature, the respective contact surface of the respective part of the attachment adapter bearing 20 is curved correspondingly. The attachment adapter 2 is mounted movably on the attachment adapter bearing 20. The surface of the top of the upper part of the attachment adapter bearing has a convex curvature, such that the attachment adapter 2 slides along an upwardly arching, outwardly curved path during a shift of the attachment adapter 2 in the anterior-posterior direction. The attachment adapter bearing 20 itself can likewise be mounted adjustably or displaceably on the leaf spring in the area of the attachment section 13, for example in a slit in order to effect a longitudinal adjustment. A clamping action on the leaf spring 10 can be effected via fastening screws of the attachment adapter 10 or via separate clamping devices, for example screws. Analogously to the attachment adapter 2 according to FIG. 2, a scale can likewise be provided on the attachment adapter bearing 20 in order to facilitate either a setting of the attachment adapter bearing 20 on the leaf spring 10 or the orientation of the attachment adapter 2 on the attachment adapter bearing 20.

Figure 12:
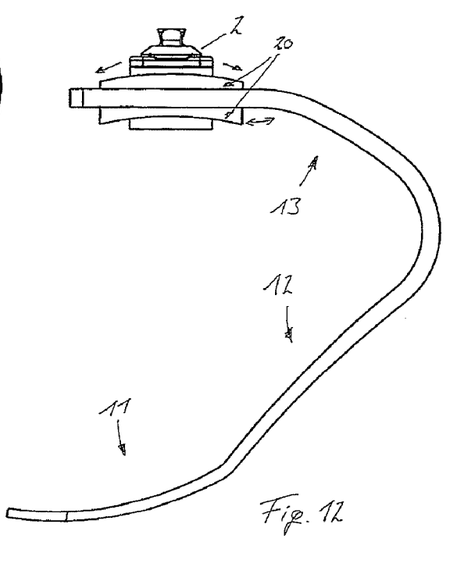
FIG. 12 shows a side view of FIG. 11.

FIG. 12 shows the variant according to FIG. 11 in a side view. It illustrates the respectively convex curvature of the foot-strike section 11 and also of the attachment adapter bearing 20 for the arcuate shifting of the attachment adapter 2 during an adjustment of the leaf spring 10 in the anterior-posterior direction. The attachment adapter bearing 20 can be shifted in the anterior-posterior direction on the leaf spring 10. Alternatively to securing the attachment adapter 2 from above, it is possible to provide a vertically oriented web on the attachment adapter bearing 20, on which web the attachment adapter 2 can be mounted displaceably and clamped. Instead of stepless shifting by way of a slit on or in the attachment adapter bearing 20, in a slit in the leaf spring 10 or in a combination thereof, it is possible to perform an adjustment in discrete steps or to carry out clamping in accordance with the leaf spring as per FIG. 10 without receiving slit.

The invention claimed is:

1. A jointless prosthetic foot, comprising:
   a leaf spring which has a distal foot-strike section, a connecting section, and a proximal attachment section which extends in an anterior-posterior direction and on which an attachment adapter can be secured;
   wherein the attachment adapter is mounted so as to be adjustable along a convexly curved path in the anterior-posterior direction, the convexly curved path having a radius of curvature with a center point arranged in the distal foot-strike section.

2. The prosthetic foot as claimed in claim 1, wherein a bearing of the attachment adapter has a convex shape.

3. The prosthetic foot as claimed in claim 2, wherein a receiving slit, extending in an anterior-posterior direction, or a receiving guide for the attachment adapter is arranged or formed in at least one of the proximal attachment section and the attachment adapter bearing.

4. The prosthetic foot as claimed in claim 1, wherein the convexly curved path is defined by the proximal attachment section.

5. The prosthetic foot as claimed in claim 1, wherein the distal foot-strike section has a convex shape.

6. The prosthetic foot as claimed in claim 1, wherein the connecting section has a concave shape.

7. The prosthetic foot as claimed in claim 1, wherein the proximal attachment section has a radius of curvature which is constant with respect to a roll-off area in the distal foot-strike section.

8. The prosthetic foot as claimed in claim 1, wherein a scale for an orientation of the anterior-posterior adjustment of the attachment adapter is arranged on at least one of the proximal attachment section, an attachment adapter bearing and the attachment adapter.

9. The prosthetic foot as claimed in claim 1, wherein the leaf spring is thicker in the proximal attachment section than in the distal foot-strike section.

10. The prosthetic foot as claimed in claim 1, wherein the leaf spring in the proximal attachment section is stiffer than in the connecting section and in the distal foot-strike section.

11. The prosthetic foot as claimed in claim 1, wherein the attachment adapter is arranged on or in the attachment section, and the attachment adapter has a contact surface with a shape corresponding to the proximal attachment section.

12. The prosthetic foot as claimed in claim 1, wherein the attachment adapter or an attachment adapter bearing is composed at least of an upper and a lower adapter part, and both upper and lower adapter parts have correspondingly shaped contact surfaces.

13. The prosthetic foot as claimed in claim 1, wherein the leaf spring has a constant material thickness in the proximal attachment section.

14. The prosthetic foot as claimed in claim 1, wherein a padding or a profiling is secured in the distal foot-strike section.

15. The prosthetic foot as claimed in claim 14, wherein the padding or the profiling covers a tip of the prosthetic foot.

16. The prosthetic foot as claimed in claim 15, wherein the tip protrudes anteriorly beyond the proximal attachment section.

17. The prosthetic foot as claimed in claim 1, wherein a set-down point of the prosthetic foot lies in front of a perpendicular line of the attachment adapter.

18. The prosthetic foot as claimed in claim 17, wherein an adjustment distance of the distal foot-strike section during the adjustment of the attachment adapter remains substantially constant with respect to the perpendicular line of the attachment adapter.

19. The prosthetic foot as claimed in claim 1, wherein an adjustment range of the attachment adapter permits a rotation of between 5° and 10°.

20. The prosthetic foot as claimed in claim 1, wherein a height of the prosthetic foot remains substantially constant when the leaf spring shifts relative to the attachment adapter in the anterior-posterior direction.

21. The prosthetic foot as claimed in claim 1, wherein the leaf spring has a first free end defined by the distal foot-strike section and a second free end defined by the proximal attachment section, and the first and second free ends are positioned forward of the connection section.

22. A jointless prosthetic foot, comprising:
   a leaf spring comprising:
      a distal foot-strike section defining a first free end of the leaf spring;
      a connecting section;
      a proximal attachment section defining a second free end of the leaf spring;
   an attachment adapter connected to the leaf spring proximate the second free end, a position of the attachment adapter being adjustable in an anterior-posterior direction;
   wherein the foot-strike section and the attachment section have a different radius of curvature in a sagittal plane, and the proximal attachment section has a radius of curvature with a center point arranged in the distal foot-strike section.

23. The prosthetic foot as claimed in claim 22, wherein the second free end of the proximal attachment section is positioned proximal of the first free end.

24. A jointless prosthetic foot, comprising:
   a leaf spring comprising:
      a distal foot-strike section defining a first free end of the leaf spring;
      a connecting section;
      a proximal attachment section defining a second free end of the leaf spring, the proximal attachment section having a radius of curvature with a center point arranged in the distal foot-strike section;
   an attachment adapter connected to the leaf spring, a position of the attachment adapter being adjustable in an anterior-posterior direction;
   wherein the foot-strike section and the attachment section have a different radius of curvature in a sagittal plane.

* * * * *